United States Patent [19]
Chari et al.

[11] Patent Number: 5,098,297
[45] Date of Patent: Mar. 24, 1992

[54] APPARATUS FOR APPLICATION OF A TOOTH DESENSITIZING COMPOSITION

[75] Inventors: Srinivas Chari, Northfield; Dennis Groat, Libertyville, both of Ill.

[73] Assignee: John O. Butler Company, Chicago, Ill.

[21] Appl. No.: 512,976

[22] Filed: Apr. 23, 1990

Related U.S. Application Data

[63] Continuation-in-part of Ser. No. 253,090, Oct. 4, 1988, abandoned.

[51] Int. Cl.⁵ .............................................. A61C 5/00
[52] U.S. Cl. ...................................... 433/215; 433/80; 604/3; 401/132
[58] Field of Search ................. 433/80, 215; 604/3; 401/132, 133, 134; 222/92; 206/818; 424/49

[56] References Cited

U.S. PATENT DOCUMENTS

| | | | |
|---|---|---|---|
| 1,822,566 | 9/1931 | Davies | 604/3 |
| 2,506,600 | 5/1950 | Kassovie | 206/818 |
| 3,993,190 | 11/1976 | Schmidgall | 401/132 |
| 4,057,621 | 11/1977 | Pashley | 424/49 |
| 4,538,990 | 9/1985 | Pashley | 433/217.1 |
| 4,631,185 | 12/1986 | Kim | 424/49 |
| 4,751,072 | 6/1988 | Kim | 424/49 |
| 4,933,171 | 6/1990 | Bristow et al. | 424/49 |

FOREIGN PATENT DOCUMENTS

1021968  3/1966  United Kingdom ............... 401/132

OTHER PUBLICATIONS

Pashley C.A. 88:55104j (1978) of U.S. Pat. No. 4,057,621.
Pashley et al., C.A. 102:31929p (1985) of J. Periodoniol. 55(9) 5225 (1984).
Pashley C.A. 104:10670y (1986) of U.S. Pat. No. 4,538,990.
Pashley C.A. 104:136022g (1986) of Arch. Oral. Biol. 30(10):751-7 (1985).

*Primary Examiner*—John J. Wilson
*Attorney, Agent, or Firm*—Laff, Whitesel, Conte & Saret

[57] ABSTRACT

A composition for the rapid desensitization of dentin and a system for its application, comprising a subsaturated aqueous solution of monopotassium monohydrogen oxalate and a disposable single-use applicator/dispenser apparatus. The apparatus includes a crushable ampule containing the desensitizing solution housed in a flexible body, with a filter which retains ample fragments but allow the solution to flow to and saturate an applicator tip or swab. The applicator may be used to treat the teeth directly, or the swab may be removed from the applicator after saturation and placed on hard-to-reach dentinal surfaces. In one embodiment, the apparatus further includes a dispensing package containing a plurality of the single-use applicators and provided with a magnetic means affixed thereto for securing the package to convenient metallic surfaces. Another embodiment includes a blister dispensing package comprising a plurality of detachable sheets which stores the applictors. The swab may be comprised of two wads pressed together, each wad being constructed of a porous spongelike material bonded to a porous plastic material. The porous plastic material may be stitched together by fiber strings.

25 Claims, 3 Drawing Sheets

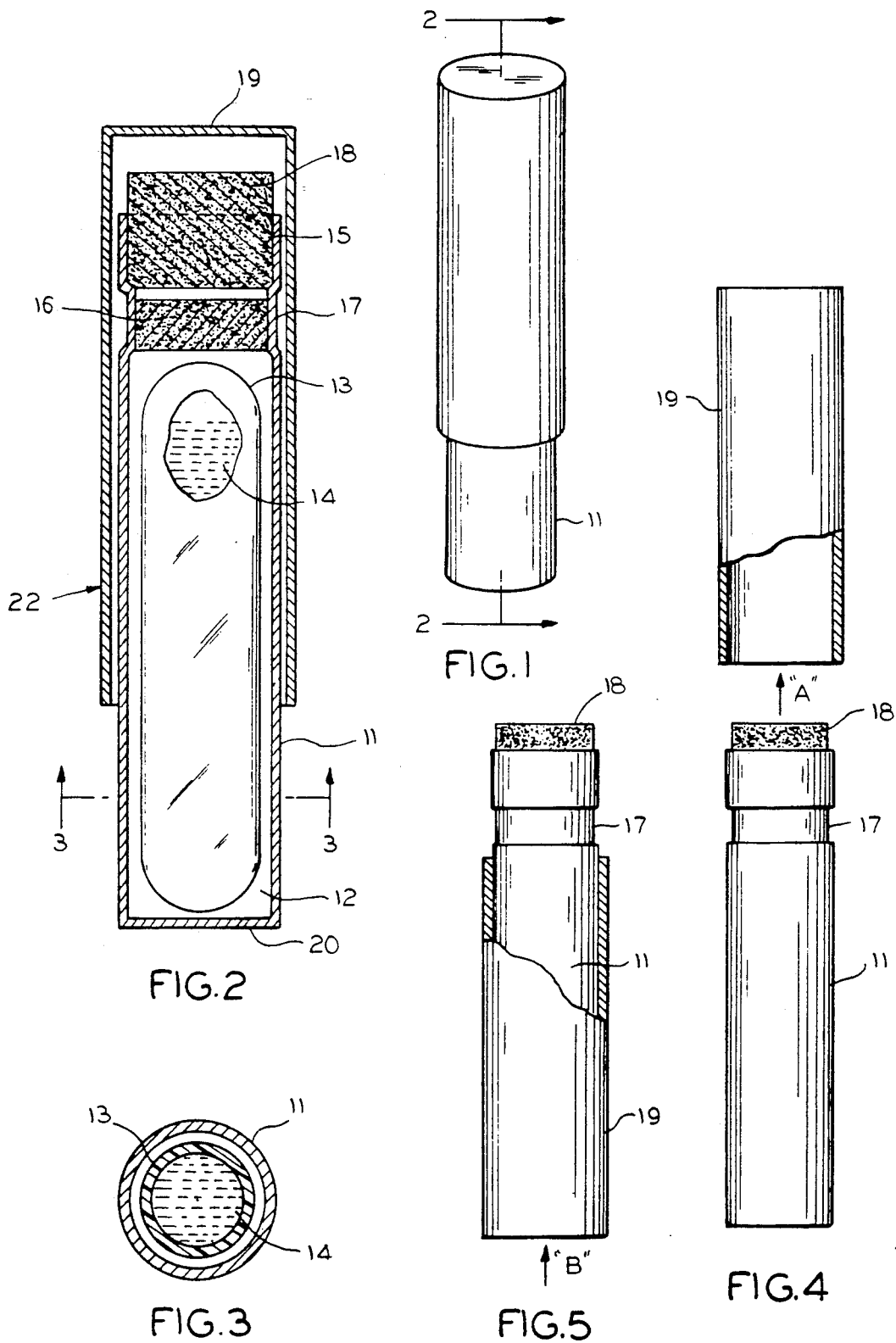

APPARATUS FOR APPLICATION OF A TOOTH DESENSITIZING COMPOSITION

This application is a continuation-in-part of application Ser. No. 253,090 filed on Oct. 4, 1988, entitled Tooth Desensitizing Composition and System, now abandoned.

BACKGROUND OF THE INVENTION

This invention relates to desensitizing teeth and more particularly to a composition, process and apparatus for this purpose.

The principal bulk of human teeth consists of dentin, a calcareous matrix surrounding the pulp and penetrated by numerous tubules. Although the peripheral one-half of the dentin appears to be without nerve endings, the movement of dentinal fluid through these tubules is believed to stimulate pain receptors found closer to the pulp. This is thought to be the mechanism responsible for dentin hypersensitivity, which commonly arises after periodontal surgery or root planing and which produces acute discomfort upon mechanical, thermal, or osmotic stimulation of the tooth (See Braennstroem et al., 1967).

Many of the efforts directed at a reduction of dentin hypersensitivity have sought to impede movement of the dentinal fluid by constricting or occluding the tubule openings. Of particular use have been compounds penetrating the dentinal tubules and causing the formation therein of crystalline precipitates which block fluid movement. Desensitizing compounds which function in this manner are the subject of U.S. Pat. No. 4,057,621 and of other patents cited therein.

A particularly promising desensitizing treatment involves the use of oxalate salts as described in U.S. Pat. Nos. 4,057,621 and 4,538,990 to induce the formation of calcium oxalate and other crystals at the tooth surface. The former '621 patent discloses, at lines 58–68 of column 2, the use of mono- and di-substituted alkali metal and ammonium oxalate solutions in concentrations at or near saturation. These saturated solutions may present problems in general use, however, as variations in shipping and/or storage temperature can bring about precipitation of the oxalate salt and an undesirable cloudiness of the preparation. The latter '990 patent, on the other hand, teaches at lines 57–64 of column 1 a two-step procedure involving the application of a neutral oxalate salt solution followed by an acidic oxalate salt solution. A drawback of such a procedure is the relative inconvenience and costliness of a multiple-step treatment, as well as the increased likelihood of confusing one solution for another. Moreover, the proposed neutral salt of choice (dipotassium oxalate) may be toxic when ingested, posing a risk in the event that over-the-counter distribution or unsupervised use by the patient is desired. Dipotassium oxalate also has been reported to have caused pain upon application.

It is, therefore, an object of the invention to provide a compound for dentin desensitization which is easy to apply without discomfort. A further object is to provide a fast-acting, single-step application which reduces cost, eliminates the potential for confusion between multiple solutions, and allows rapid and convenient desensitization without posing the risk of systemic or tissue toxicity presented by a dipotassium oxalate formulation.

Yet another object of the invention is to provide a desensitizing compound in a form which is stable during shipment and storage, and thus is suitable for commercial distribution to dental professionals and patients. It is also an object to furnish a process and apparatus for the delivery of this compound to dentinal surfaces in a practical, efficient, and economical fashion by both dental professionals and their patients, including a packaging means which enhances the convenience and usefulness of the apparatus.

SUMMARY OF THE INVENTION

The above objectives are met by the present invention. A representative composition consists of a subsaturated aqueous solution of monopotassium monohydrogen oxalate of approximately 90% of saturation concentration. The solution, which is resistant to crystallization of the solute under normal shipping and storage conditions, contains a water-soluble colorant, as well as appropriate preservative agents. When applied to the dentin for a period of one to two minutes, a relief from hypersensitivity is obtained which has been found to substantially equal the relief achieved by the earlier two-step formulations.

The apparatus which forms a part of the present invention facilitates the above process by further enabling the safe and convenient desensitization of dentin. In one embodiment of the invention, a disposable unit-dose container is provided which doubles as an applicator when facial tooth or root surfaces are treated. A cotton pellet or the like positioned so as to protrude from one end of the device can deliver the oxalate solution directly. Or, the pellet may be removed after saturation by the solution and then manipulated into less accessible treatment areas. Saturation is accomplished by squeezing the flexible tube which forms the body of the apparatus, thereby crushing an ampule housed within the body and releasing the oxalate solution therein. A colorant may be provided to indicate that the cotton tip is properly saturated, as well as, to allow the user to see which dentinal surfaces have been treated.

A further embodiment of the invention includes a blister dispensing package which stores the disposable container. The package includes a strip of detachable units, each detachable unit having a plastic film and a paper backing which are joined together. The plastic film has a blister formed therein to store the container. At one end, the plastic film has at least one rib formed therein. The rib facilitates the separation of the film from the backing for easy access to the disposable container.

The apparatus thus comprises a low cost delivery system which is easily used and, which by its nature, avoids the concerns attendant upon most multiple-dose systems, such as waste, cross-contamination, and possible toxicity from excessive dosage. Also provided are packaging means with a magnet for attachment to a metal work station, so that the disposable unit-dose container can be easily dispensed and used in the dental operation. Other advantages of the present invention will become apparent in the following detailed description of a representative embodiment.

BRIEF DESCRIPTION OF THE DRAWINGS

FIG. 1 is a perspective view of one embodiment of the apparatus of the present invention.

FIG. 2 is a longitudinal partial cross-section, taken along line 2—2 in FIG. 1, showing an elevation view of the crushable ampule with a portion cut away to show the fluid therein.

FIG. 3 is a cross-section of the body of the apparatus, taken along a plane containing the line 3—3 in FIG. 2.

FIG. 4 is a side elevation view of the embodiment of FIG. 1 showing the cover, drawn in partial cross-section, after removal from the body of the apparatus.

FIG. 5 is a side elevation view, as in FIG. 4, showing the cover, again in partial cross-section, after placement over the body of the apparatus from below.

DETAILED DESCRIPTION OF THE PREFERRED EMBODIMENT

Figure 6:
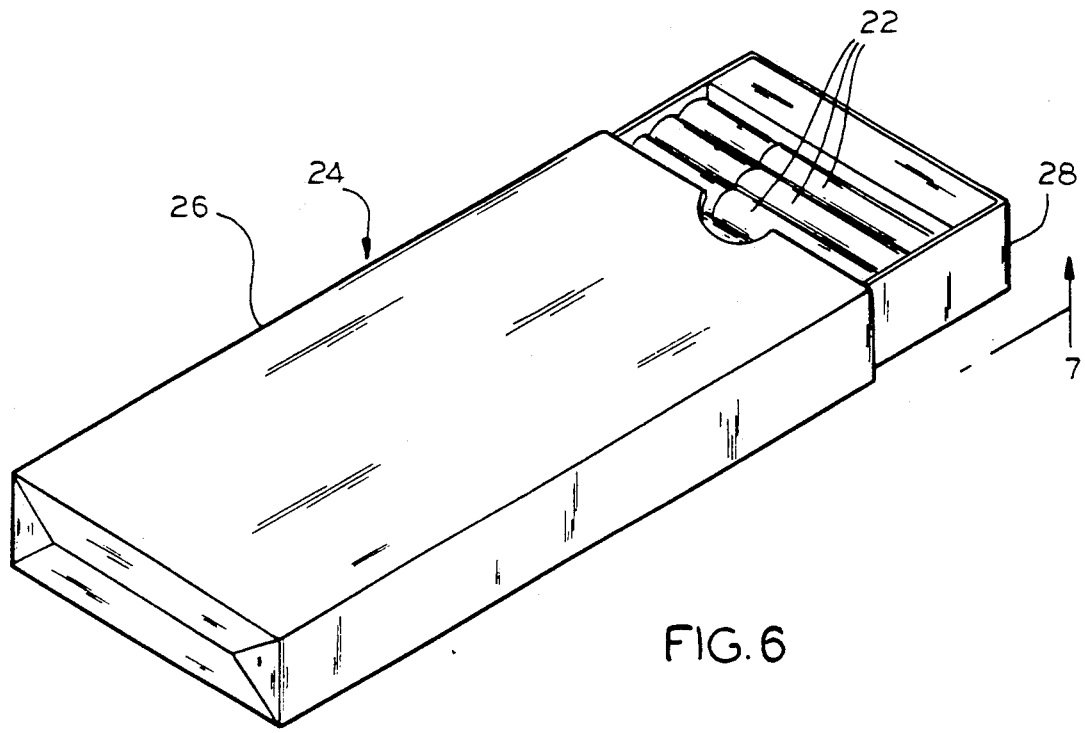
FIG. 6 is a perspective view of one embodiment of the packaging and dispensing means of the present invention.

The present invention provides an integrated system for rapid dentin desensitization comprising a desensitizing composition, a process for its use in treating dentin hypersensitivity, and an apparatus for delivery of the composition to dentinal surfaces together with an improved packaging means for the apparatus. These separate components will be better understood with reference to the following embodiments which are illustrative only and not intended to limit the scope of the invention.

In a preferred desensitizing composition, a subsaturated solution of monopotassium monohydrogen oxalate is prepared in a 2.7% w/v (weight-to-volume) ratio with deionized water. At approximately 90% of the room temperature saturation concentration, this solution remains unaffected by minor temperature fluctuations which would cause the undesirable crystallization of near-saturation oxalate solutions. The composition thus remains in a condition for immediate use following shipping and storage, without the need for agitation and/or warming to redissolve any precipitates.

The use of a subsaturated desensitizing composition is of considerable advantage, while nonetheless providing ample reduction in dentin hypersensitivity. Moreover, the selection of monopotassium over dipotassium oxalate or other treatments is supported by indications that monopotassium oxalate, applied alone, will optimally reduce dentin permeability. This effect is believed to follow from the acidity of the monopotassium composition, which can be adjusted to a pH of between 1.9 and 2.4. In this low pH range, intra-tubular formation of calcium oxalate crystals is facilitated, and occlusion of dentinal tubules is enhanced.

Further constituents of the preferred composition are a water-soluble colorant such as an FD&C Blue dye in a 1% v/v ratio, and preservatives such as methyl- and proplyparaben (also known as methyl and propyl parahydroxybenzoate) at concentrations of 0.18% and 0.02% w/v, respectively. The introduction of a colorant is especially useful, indicating thorough saturation of the applicator upon dispensing of the composition. It also serves to verify a thorough coating of the dentinal surfaces to which the composition has been applied, while remaining readily removable at the conclusion of treatment.

The above composition lends itself to a simple and effective process for dentin desensitization. Optimal and long-lasting results are obtained after treatment times of 1-2 minutes. Additionally, the packaging of the composition in a unit-dose form provides the advantages previously discussed: waste of unused desensitizing composition is eliminated, no cross-contamination of supplies can occur, and the risk of delivering an excessive and potentially toxic amount of the composition is avoided.

Application of the composition to hypersensitive dentin is facilitated by a novel apparatus for delivery of the solution. As shown in FIGS. 1-3, one embodiment of the apparatus comprises an applicator 22 having an elongated tubular body 10 of a flexible material which forms a cavity 12 and which is open at one end. Carried within the cavity 12 is a crushable ampule 13 of glass or other suitable material containing the desensitizing composition 14 in solution form. Between the ampule 13 and a neck portion 15 of the body which is adjacent the open end, a porous disc or filter 16 is positioned so as to seal the ampule 13 within the cavity 12. The porous disc 16 can be secured by a circumferential bond crimp 17 of the body 10 or by other suitable means.

Arranged against the outer surface of the porous disc 16, a pellet 18 of cotton or other suitable absorbent or dispensing material is positioned in the neck portion 15 so as to provide slightly beyond the open end of the body. An applicator tip is thereby formed which is enclosed prior to use by an outer cover 19, constructed of cardboard for example or another suitable material. Like the body 10, the cover 19 comprises an elongated tube open at one end. The cover fits over the cotton pellet 18 and extends well down the length of the body 10 providing additional protection of the ampule 13 during shipping and handling.

Advantages of this design are best revealed by the simple manner of use envisioned for the apparatus. As seen in FIGS. 4 and 5, the dispensing material or cotton pellet 18 is first exposed by pulling the outer cover 19 off of the body 10 (indicated by arrow A). The cover is then fitted over the lower body end 20 (indicated by arrow B), enlarging somewhat the diameter of the body and affording the user an improved grip. Next, the midsection of the body is squeezed to crush the ampule 13 and to release the desensitizing solution 14, which readily passes through the porous disc or filter 16 and is wicked up by the cotton pellet 18. Fragments of glass or other ampule material from the crushed ampule 13, however, are trapped by the porous disc 16 and remain behind. The colorant added to the composition provides a visual verification that the dispensing material pellet 18 is fully saturated.

The desensitizing solution can now be applied directly to the hypersensitive dentinal areas being treated. The dispensing material pellet 18 is used as an applicator tip and the body 10 as the handle of the applicator 22. Because of the small size of the applicator, envisioned to be on the order of 6 cm in length, many dentinal surfaces may be reached without difficulty. Should a treatment area be inaccessible in this manner, however, the pellet may be removed from the applicator with forceps or other suitable instrument and used to swab the dentin with the desensitizing composition.

Disc 16 safely retains the glass fragments from the crushed ampule in the cavity 12. To this end, the body 11 can be molded from a transparent or translucent plastic which allows the user to visually establish that an entire desensitizing dose has been delivered. It should also be noted that the body 11 and outer cover 19 can easily be adapted to bear product labelling and graphics where desired.

Figure 7:
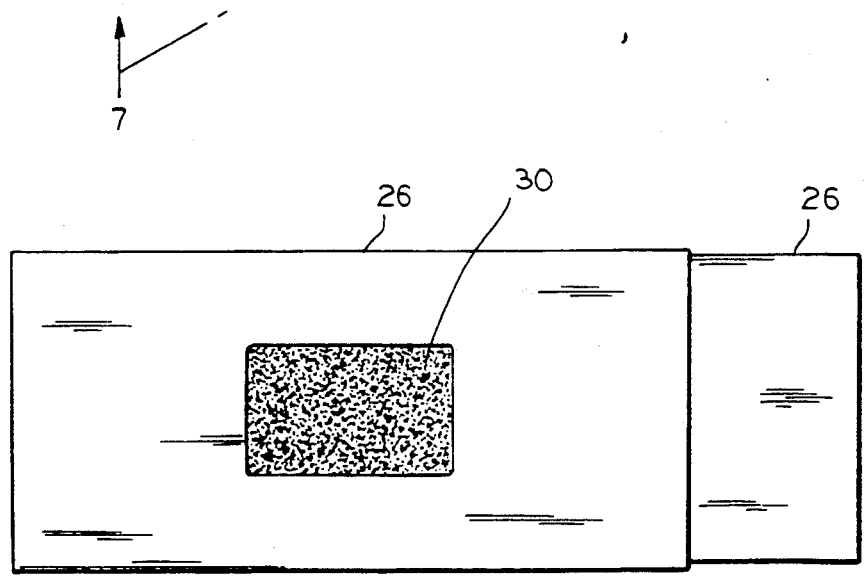
FIG. 7 is a bottom plan view of the packaging means of FIG. 6, showing a magnetic attachment means.

Shown in FIGS. 6 and 7 is an embodiment of a display and dispensing package 24 which is a further part of the desensitizing apparatus of the present invention. Package 24 comprises an outer sleeve 26 enclosing a slide-out tray 28 in which multiple applicators are placed for shipment and storage. Affixed to the back of sleeve 26, either permanently or at the user's option via an adhesive backing, is a flat plastic magnet 30.

The dispensing package 24 enhances the usefulness of the desensitizing system by allowing a user, either in the professional office or at home, to keep the system near at hand or to magnetically affix it in a convenient location. A placement of the magnet on a cabinet or other metal surface can render the applicators 12 readily accessible, or serve as a reminder to the user.

Figure 8:
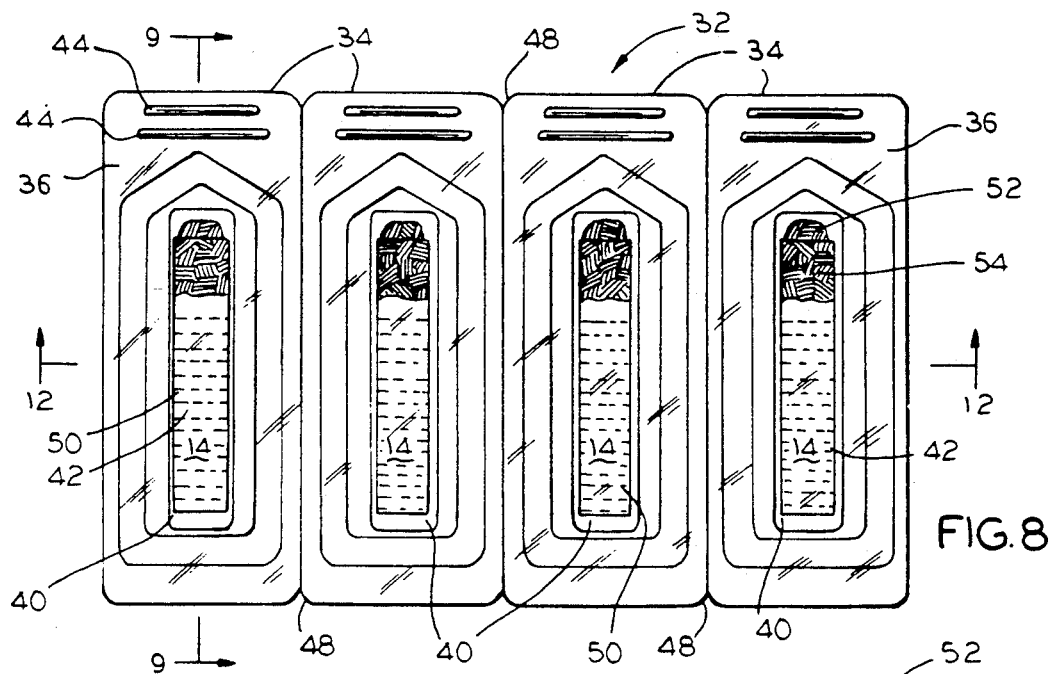
FIG. 8 is a top plan view of a strip of the blister package, in accordance with a second embodiment of this invention.
Figure 9:
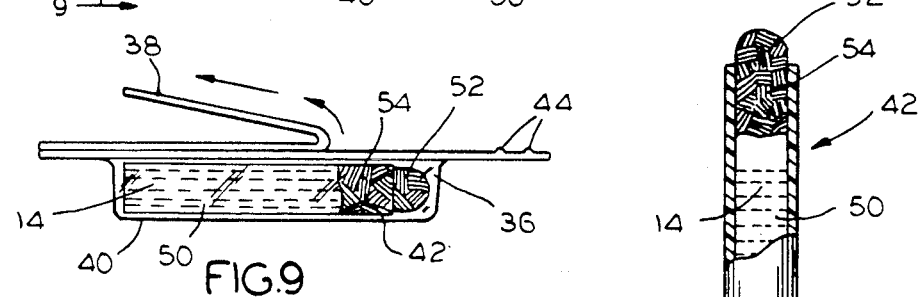
FIG. 9 is a side view of the blister package shown in FIG. 8, which has a layer peeled back to open the package.

FIGS. 8-12 reveal another embodiment of the invention. More specifically, FIG. 8 shows a strip 32 of four detachable blister packages. Each blister pack includes a plastic film 36 and a paper backing 38 which are releasably joined together in any suitable manner, as by glue, cement, heat sealing or the like. The plastic film 36 has a blister 40, which is adapted to retain a disposable container 42. At least one rib 44 is formed on an end of the plastic film to provide a plastic-to-paper separation 45 (FIG. 11) to be caught by a thumb nail.

Figure 10:
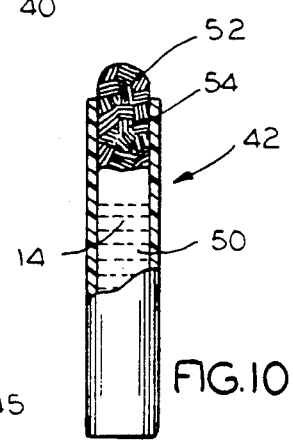
FIG. 10 is a side elevation view of the disposable container shown in FIG. 8, drawn in partial cross-section.
Figure 11:
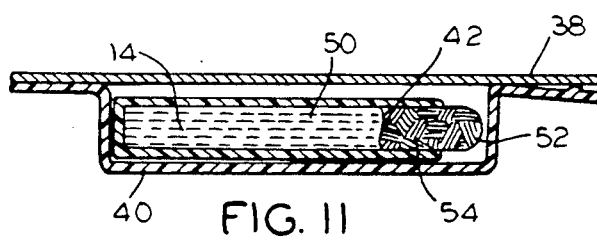
FIG. 11 is a cross-section view of the blister package similar to the view of FIG. 9, but before the package is opened.
Figure 13:
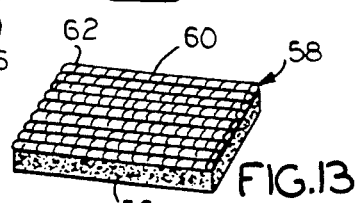
FIG. 13 shows a preferred material which is used as a swab at the open end of a tubular body.
Figure 12:
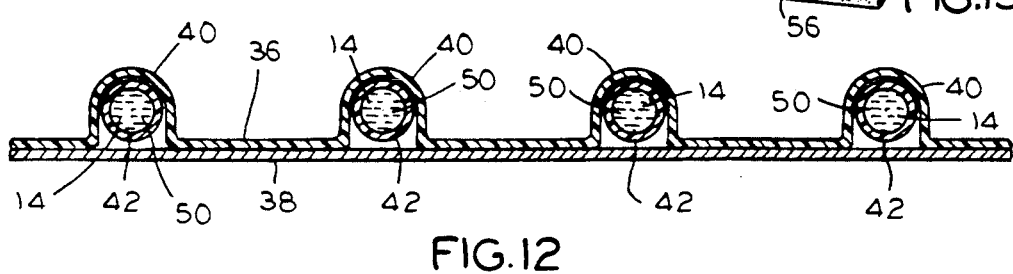
FIG. 12 is a cross-section view of a strip of the blister package taken along a plane containing the line 12—12 in FIG. 8.

The disposable container 42, as best shown in FIG. 10, preferably is cylindrical and has one open end. The container stores a crushable ampule 50 which is constructed of glass or other suitable material and which is adapted to contain the desensitizing composition in solution form. Preferably, an applicator tip or dispensing material is formed by a first wad 52 in series with a second wad 54 which are pressed together and located within one end of the container 42. Wad 52 protrudes slightly beyond the open end of the container. Each wad is comprised of a porous, spongelike material 56 (FIG. 13) and a porous plastic material 58 bonded thereto in any suitable manner as by glue, cement, or ultrasonical heating, or the like. The porous plastic material 58 comprises a plurality of fiber strands or strings 60 which are stitched together at 62 in order to form a fabric like material. Preferably both the spongelike material and the stitched fabric material pass, but do not absorb the fluid so that little or no fluid is wasted by being soaked up by the wadding material.

To use a container according to this embodiment of the invention, a detachable package 34 is detached at perforations 48. A thumb nail, or the like, is slipped into the space 45 (FIG. 11) at the end adjacent the ribs 44. An upward pressure is then applied to the paper 38 to cause separation from the plastic film forming the blister pack. This allows access to the container 42. Next, the midsection of the container is squeezed to crush the ampule 50 and to release the desensitizing solution 14, which is wicked up by wads 50, 52. The desensitizing solution can now be applied directly to the hypersensitive dentinal areas being treated.

Fragments of glass or other ampule material from the crushed ampule 50 are more effectively trapped behind wad 54. The end wad 52 forms the dispensing material swab which may be used to paint the teeth with the desensitizing material. Moreover, if desired, the dual wad system also enables the top wad 52 to be removed from the container by a use of tweezers or the like which may be used to apply the solution to hard to reach places. The remaining wad 54 continues to remain in place in order to retain the glass fragments within the container 42. The medication penetrates and is held by the spongelike dispensing material of the wads 52, 54 but not by the plastic material 58. This plastic material, however, is able to wick the solution so that it can be applied to the hypersensitive dentinal areas. As a result, all of the medication is available for application to the teeth and is not dissipated by an internal swelling of an absorbant fiber.

The dispensing package and container of the second embodiment provides an apparatus for the delivery of the compound to dentinal surfaces in a practical, efficient and economical fashion. The blister package and container allow a user to keep the system near at hand either in the professional office or at home, and also to provide an efficient and effective storage system.

With reference to the various above-described components of the apparatus of the disclosed embodiment, it is noted that uses may arise which are outside the field of dental treatment. Therefore, the applicator may deliver other solutions or compounds to surfaces other than teeth. It is envisioned that these and other variations upon the disclosure may be undertaken without departing from the scope of the invention. Therefore, the appended claims are to be construed to cover all equivalent structures involving the scope and the spirit of the invention.

What is claimed is:

1. A disposable apparatus for application of an aqueous solution of monopotassium monohydrogen oxalate to exposed dentinal surfaces, said solution being dispensed from a disposable unit-dose applicator including:
   an elongated flexible body forming a cavity and having one open end,
   a crushable sealed ampule housed in said cavity and containing said solution,
   a crushed material retainer secured to and within said flexible body and separating said cavity from said open end, said crushed material retainer comprising a porous disc filter, and
   a liquid dispensing material secured to said flexible body adjacent said crushed material retainer opposite said cavity and extending beyond said open end,
   whereby, upon squeezing of said flexible body, said ampule is crushed permitting said solution to soak through said retainer and saturate said dispensing material, thus allowing an application of said solution to accessible dentinal surfaces,
   wherein said dispensing material is a cotton pellet.

2. The apparatus of claim 1 wherein said flexible body is substantially cylindrical in shape and the ampule is glass.

3. The apparatus of claim 1 wherein after saturation said dispensing material is removable from said open end for delivery of said solution to dentinal surfaces.

4. The apparatus of claim 1 wherein said solution has a colorant whereby, upon use, saturation of said dispensing material with said solution can be visually verified.

5. The apparatus of claim 1 wherein said cover is form-fitting and capable of receiving printed material and being fitted over an opposite end of said body prior to use.

6. The apparatus of claim 1 additionally comprising a dispensing package capable of containing a plurality of said applicators.

7. The apparatus of claim 6 wherein an outer surface of said dispensing package is provided with a magnetic means for securing said package to a suitable metallic surface.

8. The apparatus of claim 6 wherein said dispensing package comprises an outer sleeve and an inner slide-out tray containing said applicators.

9. A disposable apparatus for application of an aqueous solution of monopotassium monohydrogen oxalate to exposed dentinal surfaces, said solution being dispensed from a disposable unit-dose applicator including:
an elongated flexible body forming a cavity and having one open end,
a crushable sealed ampule housed in said cavity and containing said solution,
a crushed material retainer secured to and within said flexible body and separating said cavity from said open end, said crushed material retainer comprising a porous disc filter, and
a liquid dispensing material secured to said flexible body adjacent said crushed material retainer opposite said cavity and extending beyond said open end,
whereby, upon squeezing of said flexible body, said ampule is crushed permitting said solution to soak through said retainer and saturate said dispensing material, thus allowing an application of said solution to accessible dentinal surfaces,
wherein said flexible body has a cover which is open at one end and which has a cap portion covering said dispensing material and a sleeve portion extending over said body, said cover being capable of being pulled off of said body prior to use.

10. A disposable apparatus for application of an aqueous solution of monopotassium monohydrogen oxalate to exposed dentinal surfaces, said solution being dispensed from a disposable unit-dose applicator including:
an elongated flexible body forming a cavity and having one open end,
a crushable sealed ampule housed in said cavity and containing said solution,
a crushed material retainer secured to and within said flexible body and separating said cavity from said open end, said crushed material retainer comprising a porous disc filter, and
a liquid dispensing material secured to said flexible body adjacent said crushed material retainer opposite said cavity and extending beyond said open end,
whereby, upon squeezing of said flexible body, said ampule is crushed permitting said solution to soak through said retainer and saturate said dispensing material, thus allowing an application of said solution to accessible dentinal surfaces,
wherein a circumferential crimp secures said disc in said flexible body.

11. A disposable apparatus for application of an aqueous solution of monopotassium monohydrogen oxalate to exposed dentinal surfaces, said solution being dispensed from a disposable unit-dose applicator including:
an elongated flexible body forming a cavity and having one open end,
a crushable sealed ampule housed in said cavity and containing said solution,
a crushed material retainer secured to and within said flexible body and separating said cavity from said open end, said crushed material retainer comprising a porous disc filter, and
a liquid dispensing material secured to said flexible body adjacent said crushed material retainer opposite said cavity and extending beyond said open end,
whereby, upon squeezing of said flexible body, said ampule is crushed permitting said solution to soak through said retainer and saturate said dispensing material, thus allowing an application of said solution to accessible dentinal surfaces,
wherein said cover is form-fitting and capable of receiving printed material and being fitted over an opposite end of said body prior to use and wherein said cover is cardboard.

12. A disposable apparatus for application of a dental liquid to exposed dentinal surfaces comprising an applicator including:
an elongated flexible body forming a cavity and having an open end,
a crushable sealed ampule housed in said cavity and containing said liquid,
second dispensing material secured to and within said flexible body and separating said cavity from said open end, said second dispensing material comprising a swab, and said second dispensing material adapted to retain crushed material and allow said liquid to freely pass therethrough, and
first dispensing material being a swab position adjacent said second dispensing material opposite said cavity and extending beyond said open end to absorb and retain said dental liquid, said dental liquid being an aqueous solution of monopotassium monohydrogen oxalate for application to exposed dentinal surfaces,
whereby, upon squeezing of said flexible body, said ampule is crushed permitting said liquid to pass through said second dispensing material and be absorbed by said first dispensing material, allowing an application of said liquid to a target surface.

13. A disposable apparatus for application of a dentin desensitization solution comprising an applicator including:
an elongated flexible body forming a cavity and having one open end,
a crushable sealed ampule housed in said cavity and containing said solution,
a filter secured to and within said flexible body and separating said cavity from said open end, said filter comprising a first absorbent swab, and
a second absorbent swab positioned adjacent said filter opposite said cavity and extending beyond said open end, said second absorbent swab being secured to said flexible body,
whereby, upon squeezing of said flexible body, said ampule is crushed permitting said solution to soak through said first absorbent swab and saturate said second absorbent swab, allowing application of said solution to accessible dentinal surfaces.

14. The apparatus of claim 13 wherein said flexible body is provided with a cover open at one end and having a cap portion covering said swab and a sleeve portion extending over said body, said cover capable of being pulled off of said body prior to use.

15. The apparatus of claim 13 wherein said flexible body is substantially cylindrical in shape and the ampule is glass.

16. The apparatus of claim 13 wherein said absorbent swab is a cotton pellet.

17. The apparatus of claim 13 wherein said absorbent swab, after saturation, is removable from said open end for delivery of said solution to dentinal surfaces.

18. The apparatus of claim 13 wherein said filter is a porous disc and a circumferential crimp secures said disc in said flexible body.

19. The apparatus of claim 13 wherein said solution is provided with a colorant whereby, upon use, saturation of said absorbent swab with said solution can be visually verified.

20. The apparatus of claim 13 wherein said cover is form-fitting and capable of receiving printed material and being fitted over an opposite end of said body prior to use.

21. The apparatus of claim 20 wherein said cover is cardboard.

22. The apparatus of claim 13 additionally comprising a dispensing package capable of containing a plurality of said applicators.

23. The apparatus of claim 22 wherein an outer surface of said dispensing package is provided with a magnetic means for securing said package to a suitable metallic surface.

24. The apparatus of claim 22 wherein said dispensing package comprises an outer sleeve and an inner slide-out tray containing said applicators.

25. A disposable apparatus for application of a liquid comprising an applicator including:
    an elongated flexible body forming a cavity and having an open end,
    a crushable sealed ampule housed in said cavity and containing said liquid,
    a filter secured to and within said flexible body and separating said cavity from said open end, said filter comprising a first absorbent swab, and
    a second absorbent swab positioned adjacent said filter opposite said cavity and extending said open end, said second absorbent swab being secured to said flexible body,
    whereby, upon squeezing of said flexible body, said ampule is crushed permitting said liquid to pass through said filter and saturate said second absorbent swab, allowing application of said liquid to a target surface.

* * * * *